United States Patent [19]

Zweig et al.

[11] Patent Number: 5,418,141
[45] Date of Patent: May 23, 1995

[54] TEST ARTICLES FOR PERFORMING DRY REAGENT PROTHROMBIN TIME ASSAYS

[75] Inventors: Stephen E. Zweig, Los Gatos; Sameer Sharma, Sunnyvale; Benjamin G. Meyer, Saratoga, all of Calif.

[73] Assignee: Avocet Medical, Inc., Los Gatos, Calif.

[21] Appl. No.: 238,842

[22] Filed: May 6, 1994

[51] Int. Cl.$^6$ .................. C12Q 1/56; C12N 9/48; G01N 31/22
[52] U.S. Cl. ...................... 435/13; 435/212; 422/56; 530/381; 530/384
[58] Field of Search ............... 435/13, 176, 177, 180, 435/182, 212, 214, 805; 422/56, 57, 60; 436/69; 530/381, 384

[56] References Cited

U.S. PATENT DOCUMENTS

| | | | |
|---|---|---|---|
| 4,416,812 | 11/1983 | Becker et al. | 260/112 R |
| 4,774,192 | 9/1988 | Terminiello | 436/530 |
| 5,059,525 | 10/1991 | Bartl | 435/13 |
| 5,110,730 | 5/1992 | Edington et al. | 435/69.6 |
| 5,254,350 | 10/1993 | Barrow | 424/570 |
| 5,270,451 | 12/1993 | Hawkins | 530/381 |

OTHER PUBLICATIONS

Tripodi A., Recombinant Tissue Factor as Substitute . . . Thrombosis & Haemostasis 67(1) 42–45 1992.
Hawkins P., Prothrombin Time Reagents Prepared . . . Clinical Hemostasis Review Apr. 1992.
Hawkins et al., "Prothrombin Time Reagents Prepared Using Recombinant Human Tissue Factor Produced in E. Coli", Clinical Hemostasis Review, Apr. 1992.
T. B. L. Kirkwood, "Calibration of Reference Thromboplastins and Standardisation of the Prothrombin Time Ratio", Thromb Haemostas 49(3):238–244 (1983).
S. Krishnaswamy, "The Interaction of Human Factor VIIa with Tissue Factor", J. Biol. Chem. 267(33):24696–24706 (1992).
Y. Nemerson, "Tissue Factor and Hemostasis", Blood 71(1):1–8 (1988).
J. D. Rawn, Biochemistry, Neil Patterson Publishers, pp. 219–232, Burlington N.C. 1989.
Shigematsu et al., "Expression of Human Soluble Tissue Factor in Yeast and Enzymatic Properties of Its Complex with Fator VIIa", J. Biol. Chem. 267(30):21329–21337 (1992).
Tripodi et al., "Recombinant Tissue Factor as Subsitute for Conventional Thromboplastin in the Prothrombin Time Test", Thrombosis and Haemostasis 67(1):42–45 (1992).

Primary Examiner—Michael G. Wityshyn
Assistant Examiner—Ralph Gitomer
Attorney, Agent, or Firm—Townsend and Townsend Khourie and Crew

[57] ABSTRACT

Test articles comprise a solid phase membrane having dry thromboplastin immobilized thereon or within. The thromboplastin is substantially free from substances which might cause aberrant functioning intermediate transition states as the thromboplastin is rehydrated with liquid sample. Coagulation neutral agents which facilitate rehydration of the dry thromboplastin are also provided on the solid phase membrane.

9 Claims, 3 Drawing Sheets

TEST ARTICLES FOR PERFORMING DRY REAGENT PROTHROMBIN TIME ASSAYS

BACKGROUND OF THE INVENTION

1. Field of the Invention

The present invention relates generally to prothrombin time blood coagulation testing, and more particularly to dry reagent prothrombin time test articles; and prothrombin time test methods which rely upon the rehydration of dried thromboplastin in the presence of blood or plasma.

Blood coagulation tests may be performed for a variety of purposes, including determination of the bleeding susceptibility of patients undergoing surgery and monitoring of patients undergoing anti-coagulation therapy for the prevention of blood clots. A variety of coagulation tests are presently in use. One of the most popular is the "prothrombin time" (PT) test which relies on induction of the extrinsic coagulation pathway by activation of coagulation protease factor VII by thromboplastin in a blood sample to be tested.

The extrinsic coagulation pathway results in the production of thrombin, which is a proteolytic enzyme which catalyzes the conversion of fibrinogen to fibrin. Such conversion is an essential function in the clotting mechanism.

Heretofore, such blood coagulation tests have tended to be complex, with performance generally limited to clinical laboratories. While such centralized testing may be adequate for surgical patients, visiting a doctor's office or a clinic on a regular basis to monitor anti-coagulation therapy is less acceptable. Thus the need for a convenient and practical home coagulation monitoring test is apparent.

Successful home blood tests have been devised for other chemistries, such as cholesterol and glucose. Among the most suitable devices for home use are dry reagent test devices containing all test components premixed, and preserved in a dry form suitable for long term storage. These dry reagent test devices include test strips, small plastic chambers, and the like.

Dry reagent assays typically have lower precision than liquid phase assays. This is because of structural differences between the two. Liquid phase assays have a very simple and uniform reaction zone which is formed by the walls of the vessel in which the reaction takes place. By contrast, dry reagent assays have a complex reaction zone, formed by the surfaces of the dry reaction chemicals and the support matrix. Typically, dry reagent support matrices are porous membranes or capillary gap chambers, which have higher surface to volume ratios than the reaction cuvettes typically used for liquid phase assays. Thus, test samples entering a dry reagent assay have a much greater chance of interacting with the assay components in a variable manner, resulting in a loss of precision. If the precision of the dry reagent assay is too low, the test can be rendered essentially useless for practical clinical applications.

A test's precision can best be described by the coefficient of variance, which is the ratio between the scatter in test results obtained in testing large numbers of identical samples, divided by the magnitude of the overall test signal. If the scatter in test replicates is large relative to the overall test signal, the test has a poor precision. Conversely, if the scatter in test results is small relative to the overall test signal, the test has a better precision. Thus, there are two ways to improve the precision of a test. The first is to reduce the scatter in test results while maintaining the signal magnitude, and the second is to increase the signal magnitude while keeping the scatter essentially constant. Often, the second method, increasing the magnitude of the test signal, is the most practical way to improve precision.

Blood and plasma contain a family of serine proteases that regulate the clotting process. These serine proteases are called coagulation "factors", are typically designated with Roman numerals (with an "a" suffix added if the factor is in an enzymatically active state), and operate in a precisely regulated amplification cascade to form blood clots at the site where tissue has been injured. These blood clots act to stop bleeding at the injury site. This particular mode of blood coagulation is termed the "extrinsic" coagulation pathway.

Normal tissue contains a membrane bound glycoprotein, called tissue factor, which is liberated when the tissue is injured. The extrinsic coagulation process begins when this tissue factor forms a complex with coagulation factor VII and/or VII(a). This tissue factor—factor VII(a) complex in turn activates factor X, which in concert with co-factor V, transforms the inactive prothrombin protease into the active thrombin enzyme. Thrombin then transforms fibrinogen into fibrin, which forms the actual blood clot. This process is described in detail in *Tissue Factor and Hemostasis*, Y. Nemerson, Blood 71 (1), 1–8, 1988, the full disclosure of which is incorporated herein by reference. The nomenclature in this document follows that of Nemerson. The prothrombin time test stimulates this coagulation pathway in vitro, using a tissue extract called thromboplastin to initiate the coagulation pathway.

Conventional PT assays have usually employed thromboplastin purified from an aqueous extract of acetone dried brain tissue. This crude extract contains many components. The active component of normal thromboplastin is a poorly defined mixture of factor VII reactive molecular complexes, each formed by an interaction between "tissue factor" proteins, and the mixture of brain lipids remaining after extraction. By contrast, synthetic recombinant thromboplastin (r-DNA thromboplastin) consists of a relatively simple, well defined complex formed by purified recombinant tissue factor protein, and a purified artificial lipid population.

It is known that, in liquid phase assays, different thromboplastin preparations can improve or reduce discrimination between blood samples having different prothrombin times. Those thromboplastins with a greater discrimination are termed "more sensitive." The liquid phase sensitivity of a thromboplastin preparation is graded by use of the international sensitivity index, or ISI. This ISI value is found by plotting, on a logarithmic scale, the prothrombin time seen with a thromboplastin lot in question, versus the prothrombin time values seen with a standardized lot of thromboplastin (normally defined to have an ISI value of 1). The ISI value is the slope of the resulting line, multiplied by the ISI of the reference thromboplastin.

The scale itself is somewhat non-intuitive. More sensitive thromboplastins have lower ISI numbers, typically around 1.0, and less sensitive thromboplastin lots have higher ISI numbers, typically around 2–3. The molecular explanation for the difference between lots is not totally understood at this time.

In the case of prothrombin time assays, high precision is of extreme clinical importance. Depending upon the severity of scatter, a blood sample with an actual International Normalized Ratio (INR) of 2.5 might, with an imprecise test, be reported as having an INR of 2.0 or 3.0. Such imprecision can lead to different clinical decisions. A physician might decide to increase anticoagulant dosage if the INR 2.0 result were obtained, and decrease anticoagulant dosage if an INR 3.0 result were obtained. Both decisions would have a significant impact on the patient well being, and both might be erroneous, since a "correct" test result of INR 2.5 might result in the decision not to adjust anticoagulant dosage at all.

Because of these clinical issues, methods to improve the precision of a dry reagent prothrombin time assays are thus of considerable importance to the field.

2. Description of the Background Art

Thromboplastins and tissue factors produced by recombinant DNA technology are described in U.S. Pat. Nos. 5,110,730 and 4,966,852. Methods to prepare thromboplastins with higher sensitivity for liquid phase assays are described in U.S. Pat. Nos. 5,270,451 and 4,416,812. Use of recombinant tissue factor in prothrombin time tests is described in *Recombinant Tissue Factor as Substitute for Conventional Thromboplastin in the Prothrombin Time Test*, A. Tripodi, A. Arbini, V. Chantarangkul, and P. Mannucci, Thrombosis and Haemostasis 67(1) 42–45 (1992). Use of the International Normalized Ratio (INR) for accounting for differences in sensitivity between thromboplastin types is described in *Calibration of Reference Thromboplastins and Standardization of the Prothrombin Time Ratio*, T. Kirkwood, Thromb. Haemostasis 49 (3) 238–244 (1983), and in *Requirements for Thromboplastins and Plasma used to Control Oral Anticoagulant Therapy*, WHO Expert Committee on Biological Standardization, 33rd Report, WHO Tech Rep. Ser 1983; 687:81–105. The mechanism by which tissue factor activates factor VIIa in the prothrombin time clotting cascade is discussed in *The Interaction of Human Factor VIIa with Tissue Factor*, S. Kirshnaswamy, The Journal of Biological Chemistry 267 (33) 23696–23706 (1992), the disclosures of which is incorporated herein by reference.

Dry reagent prothrombin time tests using test strips with dried thromboplastin are described in copending application Ser. No. 08/196,816 and U.S. Pat. No. 5,344,754, the full disclosures of which are incorporated herein by reference.

SUMMARY OF THE INVENTION

According to the present invention, an improved test article and method for performing dry reagent prothrombin time assays employs highly purified and well defined thromboplastin preparations. Such thromboplastin preparations are selected to maintain a high degree of sensitivity and specificity in their activation of coagulation factor VII(a) in test samples while the thromboplastin transitions from a dry state to a hydrated state. Particularly useful and advantageous are thromboplastins prepared by artificially relipidating tissue factor prepared by recombinant DNA techniques (referred to hereinafter as "recombinant thromboplastin").

Surprisingly, we have found that thromboplastin preparations having nearly identical liquid phase ISI values, can differ greatly in ISI values when incorporated into dry reagent prothrombin time assays. With purified natural thromboplastin, this effect can result in dry reagent prothrombin time tests with marginal clinical utility. By contrast, we have found that recombinant thromboplastin is much more resistant to this effect. Recombinant thromboplastins have nearly the same sensitivity (ISI value) in both liquid phase and dry reagent tests, and produce dry reagent prothrombin time assays with excellent clinical utility.

The explanation for this difference appears to result from the biochemistry of the thromboplastin reaction. It is known that the activity of tissue factor and thromboplastin is critically affected by the association of the tissue factor protein with its surrounding lipid population. Tissue factor protein in solution by itself is essentially inactive. The protein must be situated in a lipid matrix to be active. Lipids and lipoproteins exist in an aqueous phase as ordered aggregates in the form of monolayers, micelles, and bilayers. These aggregates have structures that are critically dependent upon the interaction between their hydrophobic lipid constituents, and the surrounding aqueous matrix. A more complete discussion of this effect is found in pages 219–232 of chapter 9: The structure of biological membranes, in *Biochemistry*, J. David Rawn, 1989, Neil Patterson Publishers, North Carolina, the disclosures of which are incorporated herein by reference.

In liquid phase prothrombin time assays, both purified natural and recombinant thromboplastin will exist in equilibrium with the liquid phase. In particular, the tissue factor portions and the lipid factor portions of the thromboplastin are in a relatively stable micellar distribution, and interact with a sample (factor VII) in a relatively consistent fashion. By contrast, in a dry reagent assay, the thromboplastin goes through a number of dramatic conformational rearrangements while it is being rehydrated by a sample. In particular, the lipid and protein components of the thromboplastin must transition between the dry phase, where ionic interactions dominate, and hydrophobic effects are non-existent, to a liquid phase where hydrophobic interactions are critical. In between these two phases, a number of short lived transition states are formed. These transition states, although short lived, have their own unique set of properties. An analogous transition can be seen when water is added to a dry detergent—the solution passes through an intermediate "turbid" phase before finally settling into a stable "clear" phase.

A key difference between the liquid phase and dry reagent PT assays is that the factor VII(a) component of the coagulation test sample is not exposed to the intermediate thromboplastin transition states in the liquid phase test, and thus is not influenced by them. By contrast, in a dry reagent prothrombin time test, the factor VII(a) component of the coagulation test sample is exposed to these intermediate states.

A second difference between conventional liquid phase and dry reagent PT assays, is that dry reagent test articles typically contain one or more soluble polymers or protein agents that are nominally inactive (coagulation "neutral" for a prothrombin time test) with respect to the test chemistry in a liquid assay, but which play a role in the proper functioning of the dry reagent test. Such agents may be used to modulate the uptake of liquid sample into the dry reagent carrier, to control the diffusion of the test components, to facilitate solubilization of the dry reagent test chemicals, or to facilitate the long term storage stability of the dry reagent test components. Such agents can be simple polymers, such as hydroxylpropyl cellulose, gantrez, polyvinyl alcohol, polyethylene glycol, and the like. Proteins, such as bovine serum albumin and the like are also used. Sugars, such as glucose, trehalose, polysaccharides such as starch or dextran, have also been used for these purposes. Detergents, such as Triton ® X-100, and the like have also been used.

Although required for proper dry reagent test functioning, such coagulation "neutral" agents can influence the conformational state of thromboplastin during the rehydration process. In particular, such agents can negatively impact the thromboplastin sensitivity (ability to interact with coagulation factor VII(a)) during the rehydration process. Unfortunately, for purified natural thromboplastins, some of the intermediate transition states formed a few seconds after initial rehydration appear to the prothrombin time sample as a functional thromboplastin of aberrant sensitivity. This can diminish the clinical utility of the dry reagent assay.

Unexpectedly however, we have found that dry reagent prothrombin time assays employing recombinant thromboplastin work unusually well. R-DNA thromboplastin based dry reagent assays do not exhibit the characteristic change in sensitivity typically obtained using conventional thromboplastin. As a result, these assays offer improved discrimination between samples with differing prothrombin time, without increasing intra-sample scatter. This increases the precision of the assay.

The improved performance of the prothrombin time assays employing recombinant thromboplastin appears to be directly related to the pure nature of the r-DNA reagent. The complex composition of purified natural thromboplastin results in a very large number of intermediate transition states occurring during rehydration. By contrast, the relatively simple and well defined composition of recombinant thromboplastin results in far fewer intermediate transition states during rehydration. As a result, the probability of producing an intermediate transition form of thromboplastin with aberrant sensitivity is reduced.

Alternatively, the thromboplastin may be viewed as undergoing a phase transition between a dry and liquid state. A purer and more homogeneous starting material (recombinant thromboplastin) will typically undergo a much sharper and well defined phase transition than a less pure or less homogeneous material (conventional thromboplastin).

In any event, the surprising and unpredictable result is that when dry thromboplastin which is free from substances which cause aberrant intermediate transition states as the thromboplastin is being rehydrated, particularly being free from such aberrant thromboplastin transition state substances which are found in thromboplastin purified from brain extract, is used in a prothrombin time test, the test sample will be exposed to a much smaller variety of different intermediate thromboplastin transition states, and a sharper transition between the initial "inactive" dehydrated thromboplastin, and the later active fully hydrated thromboplastin will result. Both effects are favorable, and lead to dry reagent prothrombin time assays with greater discrimination between samples with differing prothrombin time values. Such tests perform with enhanced precision.

DESCRIPTION OF TIME SPECIFIC EMBODIMENTS

Figure 1:
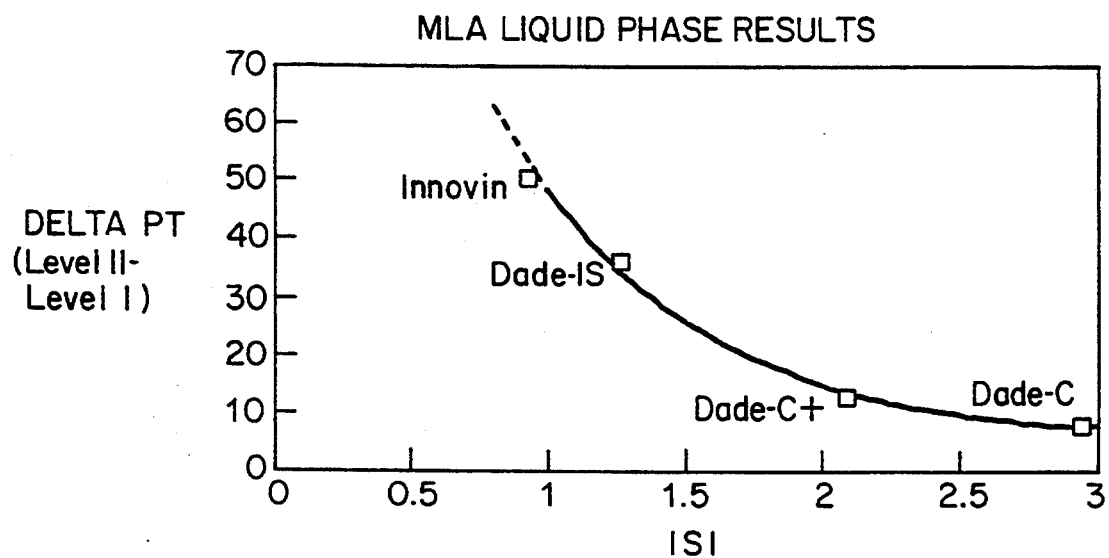
FIG. 1 shows the effect of differing thromboplastin preparations on the sensitivity of a liquid phase prothrombin time assay. On the "X" axis, are shown three normal thromboplastins, with ISI sensitivity indexes between 1.2 and 3.0. Also shown is a recombinant thromboplastin, with an ISI sensitivity index of 0.92. The "Y" axis of the graph shows the relative sensitivity of the assay, expressed as the difference in seconds between the prothrombin time value obtained with a level II control plasma, and a level I control plasma. The sensitivity of the r-DNA thromboplastin falls on the curve extrapolated from the behavior of normal thromboplastin.

The improved test articles of the present invention comprise a dry synthetic thromboplastin formulation immobilized in a test article suitable for applying undiluted blood or plasma.. The test article will usually also include dried coagulation neutral agents used to facilitate uptake and distribution of sample and can be employed with a detection mechanism that detects the time elapsed between the application of sample, and the onset of coagulation within the test article.

The dry synthetic thromboplastin is selected to maintain high sensitivity and specificity for the prothrombin time reaction while the thromboplastin is being rehydrated with the test sample, and in particular will be substantially free from substances which cause aberrant intermediate transition states as the thromboplastin is rehydrated, more particularly being free from such aberrant functioning thromboplastin transition state substances found in thromboplastin purified from brain extract. Preferably, the thromboplastin is prepared by the relipidation of a pure tissue factor preparation, using a lipid fraction that facilitates the solubilization of the tissue factor-lipid thromboplastin complex in aqueous media. In the most preferred embodiment, the thromboplastin is prepared using recombinant DNA synthesized human tissue factor. An exemplary dry synthetic thromboplastin is relipidated recombinant human tissue factor such as Innovin ™ TM thromboplastin available from Baxter Healthcare Corporation, Dade Division, Miami, Fla.

The solid phase may be a non-bibulous or bibulous structure. Non-bibulous structures will typically be impermeable structures having discrete capillary flow paths therein for receiving the blood or plasma sample being tested. The dry thromboplastin and optionally coagulation neutral agent(s) will be coated on the wall(s) of the capillary flow paths so that the thromboplastin will be rehydrated as sample is drawn therethrough by capillary action.

Bibulous structures may be composed of a material which can absorb liquid and which can contain, in dried form, the reagent(s) necessary for performing a desired assay. A wide variety of bibulous matrix materials might be used, including paper, methyl cellulose, porous polymers, and the like. In the preferred embodiment where small samples are being analyzed, a bibulous matrix will be a porous membrane structure composed of a hydrophilic (bibulous), non-swellable polymeric matrix material having pore dimensions which permit entry of blood plasma and proteins while excluding blood cells, particularly red blood cells (erythrocytes). The membrane should be composed of a single, continuous polymeric material with a foam-like structure consisting of a torturous network of channels having widths on the order of microns ($\mu m$). The tortuous network of channels is "densely packed" in that the "void volume" occupied by the empty space of the channels is an appreciable percentage of the total membrane volume, typically 10% or greater. Since all reaction chemistry, and subsequent signal generation, takes place in the void volume, a high void volume is desirable for producing a strong signal. A tortuous network of channels is desired over straight and direct pores, (such as the short, direct pores obtained with nucleopore membranes), as longer average channel lengths tend to produce an increasing isolation between the zone of the membrane where reaction chemistry is occurring, and the excess sample remaining on the surface of the membrane. This helps to render the system less sensitive to variations in applied sample volume.

The porous membrane structure will be impregnated with reagents necessary to induce coagulation in blood plasma which enters the interior of the porous matrix and to produce a detectable signal as an indication of the coagulation capability of the blood. It is particularly critical to the present invention that the polymeric matrix material of the porous membrane be substantially free from interference with the coagulation pathway which is being induced. In particular, the polymeric matrix material should be free from surface effects, interactions, and artifacts which might induce coagulation or inactivate components such as enzymes, of the initiated pathway. Unintended initiation of a coagulation pathway could lead to false positive determinations while enzyme inactivation could lead to false negative determinations. It is therefore important that the polymeric matrix material have no promoting or diminishing effect on the coagulation reactions occurring within the membrane. Criteria can be for determining if a membrane is acceptable for use in coagulation testing are set forth in detail in copending application Ser. No. 07/874,667, the full disclosure of which is incorporated herein by reference. A particularly preferred polymeric matrix material for performing blood coagulation assays is a 0.45 $\mu m$ asymmetric polysulfone membrane material available from Filterite-Memtec, 9690 Deeveco Road, Suite 7, Timonium, Md. 21093, Catalog No. BTS-25.

The coagulation neutral agents will be selected to enhance the uptake of liquid sample into the solid phase while displaying little or no effect on the measured prothrombin time. Suitable agents include proteins, such as bovine serum albumin; polymers, such as hydroxylpropyl cellulose, gantrez, polyvinyl alcohol, and polyethylene glycol; sugars, such as glucose and trehalose; polysaccharides, such as starch and dextrans; and surfactants, such as polyoxyethylene ethers.

The membrane is further processed into a test strip, with a cover structure, typically in the form of spaced-apart electrodes, separated by a gap, on the sample application side of the membrane, and a transparent strip support on the opposite side of the membrane.

In use, the strip is placed in a fluorescence detector with a strip holder stage warmed to 37° C, and with means attached to monitor the resistance drop across the electrodes when a sample is applied to the sample application side of the membrane. The fluorescence detector then takes a series of fluorescence measurements of the fluorescence seen on the underside of the membrane. More detailed criteria for constructing such test articles and detectors is set forth in detail in copending application Ser. No. 08/003,771, the full disclosure of which is incorporated herein by reference.

A thromboplastin preparation can be tested as to the presence, or absence, or aberrant functioning intermediate thromboplastin transition state substances by a functional test. To do this, a sample of the thromboplastin is dissolved in an aqueous solution, and the thromboplastin's fully hydrated performance characterized in a liquid phase prothrombin time test, using factor VII/-VII(a) containing blood or plasma samples with differing extrinsic coagulation pathway activity (prothrombin times). Next, a dehydrated sample of the thromboplastin preparation in question is incorporated into a dry reagent prothrombin time assay, which may contain one or more additional coagulation neutral agents to facilitate the function of the dry reagent assay. The performance of the dehydrated thromboplastin sample in the dry reagent assay is assessed by rehydrating it with factor VII/VII(a) containing blood or plasma samples with differing extrinsic coagulation pathway activity.

The thromboplastin sample is considered to have aberrant functioning intermediate thromboplastin transition state substances if the ability of the dry reagent assay to discriminate between samples of differing prothrombin times is impaired, relative to the liquid phase prothrombin time assay.

EXPERIMENTAL

Thrombin Substrates: Boc-Val-Pro-OH, and Tos-Gly-Pro-OH were purchased from Bachem Bioscience, Philadelphia, PA. (Boc-Val-Pro-Arg)$_2$-Rhodamine 110 and (Tos-Gly-Pro-Arg)$_2$-Rhodamine 110 were prepared by conjugating Boc-Val-Pro-OH and Tos-Gly-Pro-OH respectively onto Rhodamine-110 following the methods of Mangel, et. al. (U.S. Pat. Nos. 4,557,862 and 4,640,893).

Membranes: Asymmetric polysulfone membrane was obtained from the Memtec Corporation, Timmonium, MD.

Thromboplastin: Dade Thromboplastin C, C plus, IS, and Innovin (human thromboplastin prepared from recombinant DNA sources) were obtained from Baxter Healthcare Corporation, Miami, Fla.

Control plasma: Commercially available control plasmas were obtained from Sigma. These were C-7916 Level I Coagulation Control (activated partial thromboplastin time and prothrombin time within normal limits), C-8916 Level II Coagulation Control (mildly elevated values for activated partial thromboplastin time and prothrombin time), and Sigma C-9916 Level III Coagulation Control (severely elevated levels for activated partial thromboplastin time and prothrombin time).

The bovine serum albumin (BSA) used was Sigma A 3294, protease-free fraction V powder.

Membrane Preparation: Except where otherwise noted, reagent solutions, or "dips", were made up of 0 1 M HEPES pH 7.4, 10 mM CaCl$_2$, 20 mg/Ml Sigma protease free bovine serum albumin, 50 mg/Ml of 87–89% hydrolyzed polyvinyl alcohol (MW 13,000–23,000, Aldrich Chemical Company), lyophilized thromboplastin adjusted to obtain the equivalent of a 40% standard solution, and $2\times10^{-4}$M of the fluorescent thrombin substrate. To facilitate solubilization, the Rhodamine-110 based fluorescent thrombin substrates were pre-dissolved in a 10X stock solution of 50% isopropanol. Typically solutions were made up by first solubilizing the BSA and PVA components. Thromboplastin and thrombin substrate were added last in order to minimize possible damage to either of these biologically active components.

Membranes were coated by gently contacting one side (the larger pore, more permeable side) of the membrane to the reagent dip surface for about 5 seconds. The excess was gently squeegeed off, and the coated membrane then immediately air dried in a mechanical convection oven at 50° C. for 15 minutes. The dry membranes were then stored in sealed containers with silica gel desiccant at room temperature, or 4° C., until use.

To prevent evaporation during the meter based studies, the prepared membranes were mounted on 10 mil thick transparent styrene, using 3M 415 double sided tape, and covered with 1 mil thick aluminum foil. The sample was viewed through the transparent styrene layer.

Meter Apparatus: The dry reagent prothrombin time membranes were observed with an instrument equipped with a 550 nanometer filter with a 25 nanometer bandwidth. The specimens were illuminated by a tungsten lamp filtered through a 500 nanometer filter with a 25 nanometer bandwidth. This instrument additionally had a heated reagent stage, which kept the membrane at 37° C. throughout the assay.

Both instruments used a Siemens BPW-34B photodetector. The output from the photodetector was amplified by an instrumentation amplifier, digitized by a 12 bit analog to digital converter, and recorded on an IBM compatible personal computer.

Reference Instrument: Reference prothrombin time values were obtained using a MLA Electra 750 coagulation meter.

Example 1

Effect of different thromboplastin types on liquid and dry reagent prothrombin time tests. In this experiment, prothrombin time tests were performed using 3 normal thromboplastins, with ISI ratings between 1.2 and 2.9, and one recombinant thromboplastin, with an ISI rating of 0.92. The thromboplastins were divided into aliquots, with one aliquot used to perform a liquid phase prothrombin time assay, and the second aliquot was used to prepare dry reagent prothrombin time test strips. Prothrombin time reactions were then performed using these test strips. The thromboplastins used are shown in table 1:

TABLE 1

| Thromboplastins used in these experiments | | | |
|---|---|---|---|
| Innovin TM (r-DNA) | Dade IS | Dade C+ | Dade C |
| ISI value 0.92 | 1.2 | 2.1 | 2.9 |

Both the liquid phase assay, and the dry reagent assay, were then challenged with Sigma level I coagulation control (nominal INR of 1.0), and Sigma level II coagulation control (nominal INR of around 3.0). The liquid phase assay was run on an MLA electra 750 instrument, which determines clot formation optically by monitoring turbidity changes in a test tube style reaction cuvette.

The dry reagent assay was run on a thermostatically controlled optical fluorescence meter, as described in copending application Ser. No. 08/003,771. Other experiments (not shown) had shown that the time elapsed between the initial application of sample, and the time where the normalized fluorescence intensity first exceeded 10% of maximum (where the fluorescence intensity at Time 0 is defined to be zero, and the fluorescence intensity at maximum fluorescence is defined to be 1), designated as Time$_{10\% Max}$, or (T$_{10\%}$) gave results essentially equivalent to the classical, liquid phase, prothrombin time value. Unless otherwise stated, all dry reagent results are based upon this T10% value.

Figure 2:
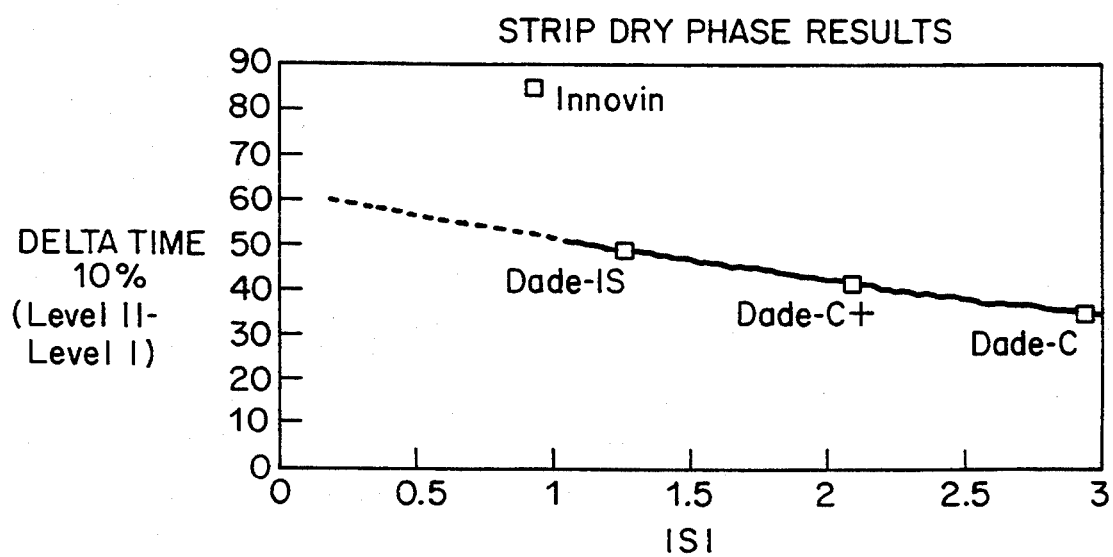
FIG. 2 shows the effect of differing thromboplastin preparations on the sensitivity of a dry reagent prothrombin time assay. On the "X" axis, are shown three normal thromboplastins, with ISI sensitivity indexes between 1.2 and 3.0. Also shown is a recombinant thromboplastin with an ISI sensitivity index of 0.92. The "Y" axis of the graph shows the relative sensitivity of the assay, expressed as the difference in seconds between the prothrombin time value obtained with a level II control plasma, and a level I control plasma. Note that the sensitivity of the recombinant thromboplastin falls off of the curve extrapolated from the behavior of normal thromboplastin.

The difference between the control level II and level I prothrombin time values, obtained by the liquid phase and dry reagent prothrombin time tests, were then plotted versus the nominal, liquid phase ISI rating of the thromboplastin reagent. The liquid phase results are shown in FIG. 1, and the dry reagent results are shown in FIG. 2. As can be seen, the liquid phase prothrombin time results follow the classical ISI sensitivity calculations. As the ISI decreases from 2.9 to 0.92, (becomes more sensitive), there is a continuous increase in the ability of the reagent system to discriminate between the level II and level I prothrombin time values. When the sensitivity curve obtained with normal thromboplastin is extrapolated to an ISI value of 0.92, the recombinant thromboplastin fits almost precisely on this curve.

By contrast, the dry reagent results are quite different. In contrast to the liquid phase results, there is only a very slight increase in sensitivity of the reagent as the normal thromboplastins are varied between ISI 1.2 and 2.9. When the sensitivity curve obtained with normal thromboplastin is extrapolated to an ISI value of 0.92, the recombinant thromboplastin shows a sharp deviation from the expected behavior. It is much more sensitive than would be expected, based upon extrapolations from normal thromboplastin activity.

Example 2

Effect of different thromboplastin types on a simplified dry reagent assay. This experiment was done to determine if the thromboplastin's deviation from ideal behavior, in the dry state, was due entirely to rehydration effects, or if it was due to interactions between the dry thromboplastin, and the other dry reagent test ingredients.

Figure 3:
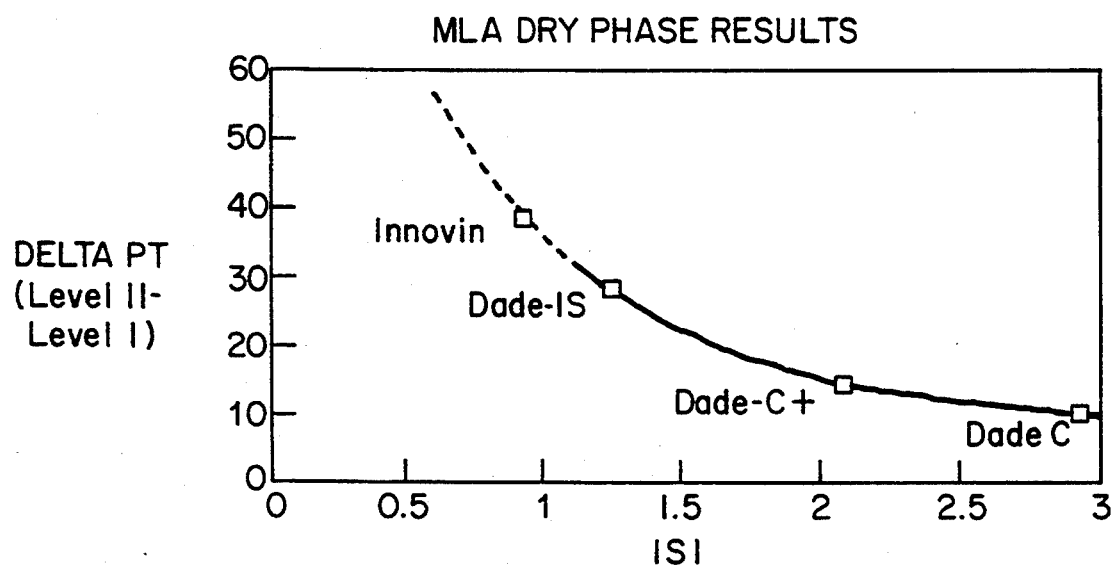
FIG. 3 shows the effect of differing thromboplastin preparations on the sensitivity of a simplified dry reagent prothrombin time assay, composed of lyophilized thromboplastin in a reaction cuvette. On the "X" axis are shown three normal thromboplastins with ISI sensitivity indexes between 1.2 and 3.0. Also shown is a recombinant thromboplastin, with an ISI sensitivity index of 0.92. The "Y" axis of the graph shows the relative sensitivity of the assay, expressed as the difference in seconds between the prothrombin time value obtained with a level II control plasma, and a level I control plasma. Note that the sensitivity of the recombinant thromboplastin remains on the curve extrapolated from the behavior of normal thromboplastin.

To do this, samples of lyophilized thromboplastin were placed directly into MLA Electra 750 reaction cuvettes, without rehydration, and without exposure to the other test chemicals typically used in the dry reagent prothrombin time test (bovine serum albumin, polyvinyl alcohol, etc.). These lyophilized thromboplastin powders were directly rehydrated with control I and control II plasma, diluted to achieve the same effective concentration as would normally be obtained if the thromboplastin had been used in its normal liquid form. The prothrombin time values obtained with thromboplastin rehydrated in the presence of sample were then determined. The results are shown in FIG. 3.

The results show that in the simplified dry reagent assay, there was a continuous increase in the ability of the reagent system to discriminate between the level II and level I prothrombin time values. When the sensitivity curve obtained with normal thromboplastin was extrapolated to an ISI value of 0.92, the recombinant thromboplastin fit almost precisely on this curve.

The results suggest that the interaction between normal thromboplastin, and the other chemicals normally incorporated into the dry reagent strip, or the strip matrix itself, contributed to the relative poor performance of the normal thromboplastin in this dry reagent assay.

Example 3

Direct comparison between the kinetics of dry reagent assays and liquid phase assays obtained using different types of thromboplastins.

Figure 4:
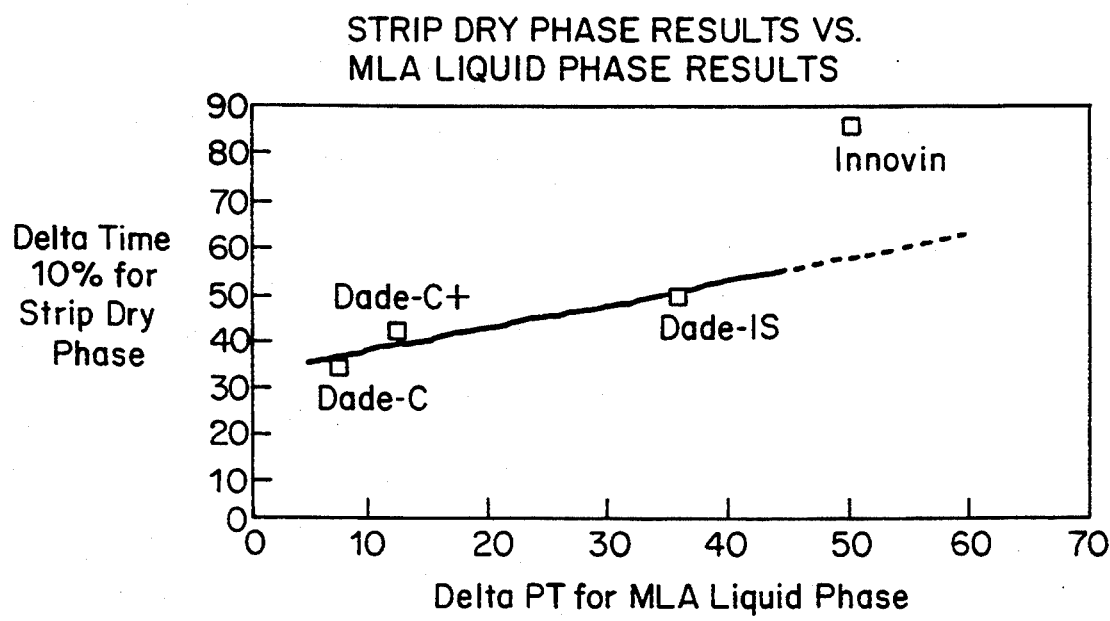
FIG. 4 directly compares the effect of differing thromboplastin preparations on the sensitivity of a liquid phase prothrombin time assay, versus a dry reagent prothrombin time test strip assay. On the "X" axis, the difference in PT times between a level I and a level II control, for a liquid phase assay, are shown, using three normal thromboplastins, and one recombinant thromboplastin. The "Y" axis shows the difference in PT times between a level I and level II control, for a dry reagent test strip assay, using the same thromboplastins. Note that again, the sensitivity of the recombinant thromboplastin falls off of the curve extrapolated from the behavior of normal thromboplastin.
Figure 5:
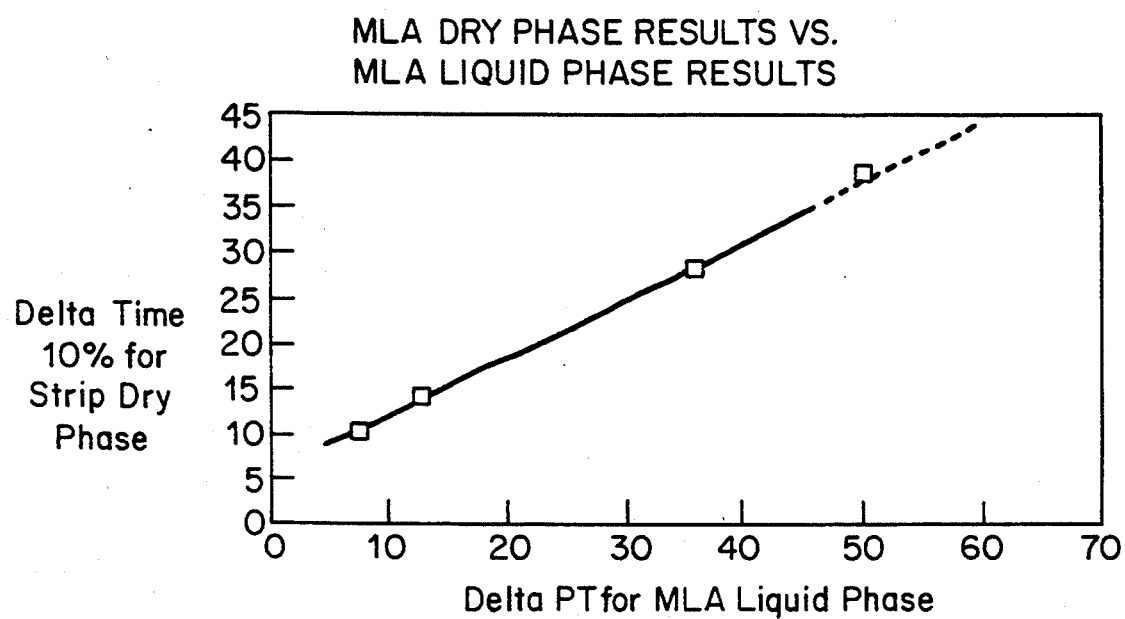
FIG. 5 directly compares the effect of differing thromboplastin preparations on the sensitivity of a liquid phase prothrombin time assay versus a simplified dry reagent prothrombin time assay. On the "X" axis, the difference in PT times between a level I and a level II control for a liquid phase assay are shown, using three normal thromboplastins and one recombinant thromboplastin. The "Y" axis shows the difference in PT times between a level I and level II control for the simplified dry reagent assay using the same thromboplastins. Note that again, for the simplified dry reagent assay, the sensitivity of the recombinant thromboplastin remains on the curve extrapolated from the behavior of normal thromboplastin.

To see if the differences between thromboplastin types could be seen directly, example 1 and 2 were repeated, this time directly comparing the differences in the prothrombin time kinetics between a level I and a level II control plasma in a liquid phase assay, to the same differences obtained in a dry reagent test strip prothrombin time assay, and the same simplified dry reagent prothrombin time assay used in example 2. The results obtained directly comparing the dry test strip assay to a liquid assay are shown in FIG. 4, and the results obtained directly comparing the simplified dry reagent assay to the liquid assay are shown in FIG. 5.

The results confirm the initial findings. When the sensitivity curve obtained with normal thromboplastin is extrapolated to an ISI value of 0.92, on the dry test strip assay, the recombinant thromboplastin shows a sharp deviation from the expected behavior. It is much more sensitive than would be expected, based upon extrapolations from normal thromboplastin activity.

Similarly, when the sensitivity curve obtained with normal thromboplastin was extrapolated to an ISI value of 0.92, with the simplified dry reagent assay, the recombinant thromboplastin fit almost precisely on this curve.

The results again suggested that the interaction between normal thromboplastin, and the other chemicals normally incorporated into the dry reagent strip, or the strip matrix itself, contributed to the relative poor performance of the normal thromboplastin in this dry reagent assay.

Example 4

Effect of different thromboplastin types on the precision of dry reagent prothrombin time assays. In this experiment, reagent strips were made up, and tested with ten replicates of Sigma level I and level II control plasma. The predicted INR values obtained from these assay were then calculated using the equation:

$$INR = (Time_{10\% \, max}/Time_{ref})Isl$$

Where Time10% max is the time required for the level II control plasma to initially develop a fluorescence intensity of 10% of its maximal level (which corresponds closely to a classical PT time in this assay), $Time_{ref}$ is the time required for the normal level I control plasma to develop a fluorescence intensity of 10% of its maximal level (corresponds closely to a control PT time in this assay), and the ISI value is chosen to properly calibrate the performance of the particular lot of strips to reference plasmas with known INR values.

The coefficient of variance (CV) in the INR results obtained with the four strip lots is shown below: This was obtained using ten replicates of control II plasma. To see if the effect was distorted by outliers, the most extreme outlier from each sample was discarded, and the CV's recomputed. This is shown in Table 2.

TABLE 2

| | CV's of dry reagents prepared with different thromboplastin types. | | | |
|---|---|---|---|---|
| | Innovin TM | Dade IS | Dade C+ | Dade C |
| Nominal ISI | 0.92 | 1.2 | 2.1 | 2.9 |
| CV: (10 reps) | 1.83% | 4.22% | 3.02% | 2.92% |
| CV: (best 9) | 1.39% | 2.35% | 2.66% | 2.23% |

Note that the dry reagent assay using recombinant thromboplastin had significantly better precision than the dry reagent assays that used normal thromboplastin, even though the liquid phase ISI rating of the recombinant thromboplastin was nearly identical to the liquid phase ISI rating of the Dade IS formulation.

Example 5

Effect of different thromboplastin types on the precision obtained with a dry reagent prothrombin time test strip, in a clinical study. In this experiment, two batches of prothrombin time test strips were made up as previously described, using either Dade Innovin TM recombinant thromboplastin, or Dade C normal thromboplastin. These strips were then used in a 25 patient clinical study. Two replicate samples from each patient were run on each thromboplastin formulation, and the agreement between each replicate sample was computed. For the recombinant thromboplastin reagent, the $R^2$ correlation coefficient between the two replicates was 0.965. By contrast, the $R^2$ correlation coefficient between the two replicates obtained using the normal thromboplastin formulation was only 0,663.

What is claimed is:

1. A test article for performing dry reagent prothrombin time assays, said test article comprising
   a solid phase matrix;
   dry thromboplastin immobilized on or within the solid phase matrix, wherein the thromboplastin is substantially free from substances found in thromboplastin purified from brain extract which cause aberrant functioning intermediate transition states as the thromboplastin is rehydrated with liquid sample; and
   coagulation neutral agents which facilitate rehydration of the thromboplastin upon contact of the solid phase matrix with the liquid sample.

2. A test article as in claim 1, wherein the dry thromboplastin is relipidated recombinant tissue factor.

3. A test article as in claim 1, wherein the coagulation neutral agents are selected from the group consisting of albumins, water soluble polymers, and surfactants.

4. A test strip comprising:
   a permeable membrane having an application face and an indicator face in lateral opposition, said membrane being substantially free from an interference with a thromboplastin-initiated and factor VII or VIIa mediated coagulation pathway; coagulation neutral agents which facilitate liquid sample uptake and distribution into the membrane;
   dry thromboplastin impregnated within the membrane, wherein the thromboplastin is substantially free from substances found in thromboplastin purified from brain extract which cause aberrant intermediate transition states as the thromboplastin is rehydrated with liquid sample; and
   a substrate impregnated within the membrane, which substrate produces a detectable signal upon activation by a component of the coagulation pathway; whereby coagulation factor VII or VII(a) containing samples may be applied to the application face of the membrane in order to produce the detectable signal on the indicator face as a result of activation of the substrate by the coagulation pathway component.

5. The test strip as in claim 4, wherein the dry thromboplastin is relipidated recombinant tissue factor.

6. The test strip as in claim 4, wherein the coagulation neutral agents are selected from the group consisting of albumins, water soluble polymers, and surfactants.

7. An improved prothrombin time assay of the type wherein a blood or plasma sample is applied to a solid phase matrix to contact dry thromboplastin to initiate a detectable reaction, wherein the improvement comprises providing a coagulation neutral agent within the matrix and contacting a dry thromboplastin which is substantially free from substances found in thromboplastin purified from brain extract which cause aberrant functioning transition states as the thromboplastin is rehydrated with the sample.

8. An improved prothrombin time assay as in claim 7, wherein the dry thromboplastin is relipidated recombinant tissue factor.

9. An improved prothrombin time assay as in claim 7, wherein the coagulation neutral agent is selected from the group consisting of albumins, water soluble polymers, and surfactants.

* * * * *

US005418141C1

(12) EX PARTE REEXAMINATION CERTIFICATE (7090th)

United States Patent
Zweig et al.

(10) Number: US 5,418,141 C1
(45) Certificate Issued: Oct. 6, 2009

(54) TEST ARTICLES FOR PERFORMING DRY REAGENT PROTHROMBIN TIME ASSAYS

(75) Inventors: Stephen E. Zweig, Los Gatos, CA (US); Sameer Sharma, Sunnyvale, CA (US); Benjamin G. Meyer, Saratoga, CA (US)

(73) Assignee: Beckman Coulter, Inc., Fullerton, CA (US)

Reexamination Request:
No. 90/009,011, Jan. 31, 2008

Reexamination Certificate for:
Patent No.: 5,418,141
Issued: May 23, 1995
Appl. No.: 08/238,842
Filed: May 6, 1994

(51) Int. Cl.
*C12Q 1/56* (2006.01)
*C12N 9/48* (2006.01)
*G01N 31/22* (2006.01)
*A61K 38/11* (2006.01)
*A61K 38/48* (2006.01)

(52) U.S. Cl. ............................ 435/13; 435/212; 422/56; 530/381; 530/384

(58) Field of Classification Search ........................ None
See application file for complete search history.

(56) References Cited

U.S. PATENT DOCUMENTS

| 2,408,535 A | 10/1946 | Smith |
| 3,983,004 A | 9/1976 | Trobisch et al. |
| 4,129,417 A | 12/1978 | White |
| 4,416,812 A | 11/1983 | Becker et al. |
| 4,458,015 A | 7/1984 | Jering et al. |
| 4,557,862 A | 12/1985 | Mangel et al. |
| 4,618,476 A | 10/1986 | Columbus |
| 4,640,893 A | 2/1987 | Mangel et al. |
| 4,755,461 A | 7/1988 | Lawson et al. |
| 4,756,884 A | 7/1988 | Hillman et al. |
| 4,761,381 A | 8/1988 | Blatt et al. |
| 4,774,192 A | 9/1988 | Terminiello et al. |
| 4,788,152 A | 11/1988 | Doeding et al. |
| 4,849,340 A | 7/1989 | Oberhardt |
| 4,855,240 A | 8/1989 | Rosenstein et al. |
| 4,935,346 A | 6/1990 | Phillips et al. |
| 4,943,522 A | 7/1990 | Eisinger et al. |
| 4,963,498 A | 10/1990 | Hillman et al. |
| 4,966,852 A | 10/1990 | Wun et al. |
| 4,978,503 A | 12/1990 | Shanks et al. |
| 5,059,525 A | 10/1991 | Bartl et al. |
| 5,096,836 A | 3/1992 | Macho et al. |
| 5,110,727 A | 5/1992 | Oberhardt |
| 5,110,730 A | 5/1992 | Edgington et al. |
| 5,145,784 A | 9/1992 | Cox et al. |
| 5,254,350 A | 10/1993 | Barrow et al. |
| 5,260,195 A | 11/1993 | Azhar et al. |
| 5,270,451 A | 12/1993 | Hawkins et al. |
| 5,314,695 A | 5/1994 | Brown |
| 5,344,754 A | 9/1994 | Zweig |
| 5,350,676 A | 9/1994 | Oberhardt et al. |
| 5,418,143 A | 5/1995 | Zweig |
| 5,554,531 A | 9/1996 | Zweig |
| 5,580,744 A | 12/1996 | Zweig |
| 5,625,036 A | 4/1997 | Hawkins et al. |
| 6,060,323 A | 5/2000 | Jina |
| 6,061,128 A | 5/2000 | Zweig et al. |
| 6,629,057 B2 | 9/2003 | Zweig et al. |
| 6,790,632 B2 | 9/2004 | Zweig |
| 7,072,035 B2 | 7/2006 | Zweig et al. |
| 7,166,208 B2 | 1/2007 | Zweig |
| 2005/0206875 A1 | 9/2005 | Zweig et al. |

FOREIGN PATENT DOCUMENTS

| CA | 2188437 | 8/2007 |
| EP | 0 638 127 | 8/2000 |
| EP | 0 758 401 | 12/2006 |
| WO | WO-88/07543 | 10/1988 |
| WO | WO-89/10788 | 11/1989 |
| WO | WO-92/08479 | 5/1992 |
| WO | WO-93/07492 | 4/1993 |
| WO | WO-93/22453 | 11/1993 |
| WO | WO-95/30770 | 11/1995 |
| WO | WO-2006/067504 | 6/2006 |
| WO | WO-2006/119203 | 11/2006 |

OTHER PUBLICATIONS

Bader et al., Thrombosis and Haemostasis (1994) 71(3):292–299.
Hawkins and Pelzer, "Prothrombin Time Reagents Prepared Using Recombinant Human Tissue Factor Produced in E. Coli" Clinical Hemostasis Review (Apr. 1992).
O'Brien et al., J. Clin. Invest. (1988) 82:206–211.
Paborsky et al., Biochemistry (1989) 28:8072–8077.
Tripodi et al., Thrombosis and Haemostasis (1992) 67:42–45.
Proprietor's Submissions in Response to the Oppositions, from Opposition against EP Patent No. 0 758 401, submitted Jul. 24, 2008.
Ansell et al., Chest (2001) 119:22S–38S.
Cullis et al., "Physical properties and functional roles of lipids in membranes" in Biochemistry of Lipids, Lipoproteins and Membranes, Vance and Vance (eds.), (1996) Chapter 1, pp. 1–17.
Della Valle et al., Ann. Med. Interne. (1996) 147:10–14.
Description of Thrombotest (PT–INR) reagent, from http://www.axis–shield–poc.com/esite/esite.nsf/pub/BLOH66JHC?Open, visited Apr. 17, 2008.
Donlon, Letters from the Department of Health & Human Services re: Biotrack Protime Test Prothrombin Time Test, dated May 23, 1986.
FDA, Enforcement Report dated Nov. 18, 1998 re: Biotrack and Coumatrak brand Protime Test Cartridges.
Finazzi et al., Thrombosis and Haemostasis (1994) 72(6):804–807.

(Continued)

*Primary Examiner*—Brenda Brumback

(57) ABSTRACT

Test articles comprise a solid phase membrane having dry thromboplastin immobilized thereon or within. The thromboplastin is substantially free from substances which might cause aberrant functioning intermediate transition states as the thromboplastin is rehydrated with liquid sample. Coagulation neutral agents which facilitate rehydration of the dry thromboplastin are also provided on the solid phase membrane.

OTHER PUBLICATIONS

Hirsh et al., Chest (1989) 95(2):5S–11S.
Hirsh et al., Journal of the American College of Cardiology (2003) 41:1633–1652.
Hoppensteadt et al., Laboratory Medicine (1995) 26(3):198–203.
Kitchen et al., Thrombosis and Haemostasis (1996) 76(3):372–376.
Kolde et al., Klin. Lab (1993) 39:767–776.
MDDI Reports (Aug. 15, 1994) p. 9–10 referencing FDA panel meeting on home prothrombin time.
Roussi et al., Thrombosis and Haemostasis (1994) 72(5):698–704.
Tejidor et al., Circulation (1991) 84(4):598.
Tripodi et al., Thrombosis and Haemostasis (1994) 72(2):261–267.
Tripodi et al., Thrombosis and Haemostasis (1994) 79(2):439–443.
U.S. Food and Drug Administration, proceedings from the Hematology and Pathology Devices Panel Meeting, Aug. 5, 1994, Rockville, MD.
Vu et al., Thrombosis and Haemostasis (1993) p. 663, Abstract No. 437.
Vu et al., Thrombosis and Haemostasis (1993) p. 663, Abstract No. 438.
Communication of Notices of Opposition, EP Patent No. 0 638 127, dated Jul. 10, 2001.
Observations on the Grounds of Opposition, EP Patent No. 0 638 127, dated Mar. 20, 2002.
Summons to Attend Oral Proceedings, EP Patent No. 0 638 127, dated Dec. 19, 2003.
Further submissions provided by the Opponent, EP Patent No. 0 638 127, dated Feb. 26, 2004.
Minutes of the Oral Proceedings held on Apr. 28, 2004, EP Patent No. 0 638 127.
Decision Rejecting the Opposition, EP Patent No. 0 638 127, dated Jun. 16, 2004.
Statement setting out the Grounds of Appeal, EP Patent No. 0 638 127, dated Oct. 13, 2004.
Submissions by Beckman Coulter, Inc. in Answer to the Statement of Grounds of Appeal lodged by Roche Diagnostics GmbH, EP Patent No. 0 638 127, dated Apr. 22, 2005.
Letter dealing with oral proceedings during the appeal procedure, with 9 Auxiliary Requests, EP Patent No. 0 638 127, dated Sep. 20, 2005.
Request for Entry into the European Phase, EP Application No. 93912264.4, dated Oct. 4, 1994.
Supplementary European Search Report, EP Application No. 93912264.4, mailed on Jan. 31, 1997.
Examination Report, EP Application No. 93912264.4, dated Jan. 5, 1999.
Reply to Examination Report, EP Application No. 93912264.4, dated Jul. 5, 1999.
Communication Under 51(4) EPC, EP Application No. 93912264.4, dated Nov. 10, 1999.
Decision to Grant a European Patent Pursuant to Article 97 (2) EPC, EP Application No. 93912264.4, dated Jul. 13, 2000.
Response to Notice to File Corrected Application Papers from U.S. Appl. No. 11/089,279, filed Jun. 2, 2005.
Non–Final Office Action from U.S. Appl. No. 11/089,279, mailed on Aug. 29, 2005.
Amendment from U.S. Appl. No. 11/089,279, filed Nov. 29, 2005.
Notice of Allowance from U.S. Appl. No. 11/089,279, mailed on Feb. 14, 2006.
Request for Entry into the European Phase, EP Patent No. 0 758 401, dated Oct. 23, 1996.
Supplementary European Search Report, EP Patent No. 0 758 401, dated Jun. 16, 2004.
Communication Pursuant to Article 96 (2) EPC, EP Patent No. 0 758 401, dated Sep. 21, 2004.
Claim Amendments, EP Patent No. 0 758 401, dated Feb. 1, 2005.
Communication Pursuant to Article 96 (2) EPC, EP Patent No. 0 758 401, dated Apr. 1, 2005.
Claim Amendments, EP Patent No. 0 758 401, dated Aug. 10, 2005.
Summons to Attend Oral Proceedings, EP Patent No. 0 758 401, dated Dec. 5, 2005.
Letter dealing with oral proceedings, with Main Request and Auxiliary Request, EP Patent No. 0 758 401, dated Jan. 23, 2006.
Communication Under 51(4) EPC, EP Patent No. 0 758 401, dated Mar. 28, 2006.
Communication Under 51(4) EPC, EP Patent No. 0 758 401, dated Jun. 2, 2006.
Decision to Grant a European Patent Pursuant to Article 97 (2) EPC, EP Patent No. 0 758 401, dated Nov. 16, 2006.
510(k) Summary of Safety and Effectiveness, Dade Innovin K974343 (1997).
510(k) Summary of Safety and Effectiveness, Dade Innovin K935702 (1993).
Abbott i–STAT Prothrombin Time test package insert, dated Jun. 11, 2008.
Brien et al., Thrombosis and Haemostasis (1994) 72(6):986–987.
Friedly, Science (1996) 271:1800–1801.
Lammle et al., Schweiz. Med. Wochenschr. (1989) 119(6):178–83.
Konigsbert and Nemerson, Cell (1988) 52:639–640.
Mann et al., Blood (1990) 76:1–16.
Morrissey, Science (1996) 272:1085.
Oberhardt et al., Clin. Chem. (1991) 37(4):520–526.
Rose et al., Arch. Pathol. Lab. Med. (1993) 117:611–617.
510(k), Avocet PT Test System, K980839 (1998).
510(k), Biotrack Protime Test Prothrombin Time Test, K860721 (1986).
510(k), Cardiovascular Diagnostics TAS, K882456 (1988).
Arnout et al., British Journal of Haematology (1994) 87:94–99.
Avocet AvoSure PT, Patient Self–Testing System Prothrombin Time Test Strips, 3 pages.
AvoSure PT Pro+, Prothrombin Time System, User's Manual, pp. 20–25.
Barcelona et al., Thrombosis and Haemostasis (1996) 75:480–490.
Brien et al., "Discrepant Results in INR Testing," in Letters to the Editor, Thrombosis and Haemostasis (1994) 72(6):986–987.
Clinical and Laboratory Standards Institute, document H47–A2 "One–Stage Prothrombin Time (PT) Test and Activated Partial Thromboplastin Time (APTT) Test; Approved Guideline—Second Edition" vol. 28, No. 20 (2008).

Clinical and Laboratory Standards Institute, document H21–A5 "Collection, Transport, and Processing of Blood Specimens for Testing Plasma–Based Coagulation Assays and Molecular Hemostasis Assays; Approved Guideline—Fifth Edition" vol. 28, No. 5 (2008).

Cunningham, Am J Clin Path (1994) 102(1):128–133.

Dade, Thromboplastin C Dried Rabbit Brain Thromboplastin with Calcium, 1987, 2 pages (package insert).

Dade, Thromboplastin C Dried Rabbit Brain Thromboplastin with Calcium, 4 pages (package insert).

Dade Innovin II, draft package insert from K935702, 6 pages.

Duncan et al., Thrombosis and Haemostasis (1994) 72:84–88.

Hirsch et al., Circulation (2003) 107:1692–1711.

Horsti, "Prothrombin Time: Evaluation of Determination Methods" Academic Dissertation, University of Tampere, Finland (2002).

Kolde, Haematologica (1995) 80(Supp to No. 2):7–13.

Kolde et al., Thrombosis and Haemostasis (1993) 69(6):A2069.

Merenbloom and Oberhardt, Clin. Chem. (1995) 41(9):1385–1390.

Moriarty et al., Pathology (1990) 22:71–76.

NCCLS, document H1–A5 "Tubes and Additives for Venous Blood Specimen Collection; Approved Standard—Fifth Edition" vol. 23, No. 33 (2003).

Oberhardt, Clin. Chem. (1993) 39(9):1982–1984.

Pi et al., J. Clin. Pathol. (1995) 48:13–17.

Poller et al., British Journal of Haematology (1994) 86:112–117.

Poller, "The Prothrombin Time" World Health Organization (1998).

Thomson et al., J. Clin. Pathol. (1990) 43:679–684.

Tripodi et al., Thrombosis and Haemostasis (1993) 70(6):921–924.

Tripodi et al., Thrombosis and Haemostasis (1997) 778:855–858.

Van Den Besselaar, Thrombosis and Haemostasis (1993) 70(5):794–799.

Van Den Besselaar, Haemostasis (1996) 26(Suppl. 4):248–265.

Zorn et al., Thrombosis and Haemostasis (1993) 69(6):A2068.

Zweig et al., Biomedical Instrumentation and Technology (1996) 245–256.

Anderson et al., Arch. Intern. Med. (1993) 153:1441–1447.

Foulis et al., Coagulation and Transfusion Medicine (1995) 103:98–102.

Jennings et al., J. Clin. Pathol. (1991) 44:950–953.

Lucas et al., A.J.C.P. (1987) 88(4):442–446.

Mcurdy and White, Arch. Intern. Med. (1992) 152:589–592.

White et al., Southern Medical Journal (1994) 87(2):206–210.

Zweig, "Dry Reagent Prothrombin Time and Other Hemostasis Methods" (2002) Chapter 5, pp. 57–66.

Conner et al., PNAS USA (1983) 80:278–282.

International Search Report for PCT/US95/05586, mailed on Jul. 31, 1995, 2 pages.

Kirkwood, Thromb. Haemostas. (1983) 49(3):238–244.

Krishnaswamy, J. Biol. Chem. (1992) 267(33):23696–23706.

Nemerson, Blood (1988) 71:1–8.

Rawn, Biochemistry, Neil Patterson Publishers, Burlington N.C. (1989) pp. 219–232.

Shigematsu et al., J. Biol. Chem. (1992) 267(30):21329–21337.

WHO Expert Committee on Biological Standardization, 33$^{rd}$ Report, "Requirements for Thromboplastins and Plasma used to Control Oral Anticoagulant Therapy", WHO Tech Rep. Ser. (1983) 687–81–105.

Court Docket from PACER for *Beckman Coulter, Inc.* v. *Hemosense, Inc.*, Case No. 5:07–cv–.

Communication of Notices of Opposition (R. 57)(1)EPC) against EP 0 758 401 dated Jan. 14, 2008.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7–9 is confirmed.

Claims 1 and 4 are determined to be patentable as amended.

Claims 2, 3, 5 and 6, dependent on an amended claim, are determined to be patentable.

New claims 10–19 are added and determined to be patentable.

1. A test article for performing dry reagent prothrombin time assays, said test article comprising
   a solid phase matrix;
   dry thromboplastin immobilized on or within the solid phase matrix, wherein the thromboplastin is substantially free from substances found in thromboplastin purified from brain extract which cause aberrant functioning intermediate transition states as the thromboplastin is rehydrated with [liquid] *a blood or plasma* sample; and
   coagulation neutral agents which facilitate rehydration of the thromboplastin upon contact of the solid phase matrix with the [liquid] *blood or plasma* sample.

4. A test strip comprising:
   a permeable membrane having an application face and an indicator face in lateral opposition, said membrane being substantially free from an interference with a thromboplastin-initiated and factor VII or VIIa mediated coagulation pathway; coagulation neutral agents which facilitate liquid sample uptake and distribution into the membrane;
   dry thromboplastin impregnated within the membrane, wherein the thromboplastin is substantially free from substances found in thromboplastin purified from brain extract which cause aberrant intermediate transition states as the thromboplastin is rehydrated with [liquid] *a blood or plasma* sample; and
   a substrate impregnated within the membrane, which substrate produces a detectable signal upon activation by a component of the coagulation pathway;
   whereby coagulation factor VII or VII(a) containing *blood or plasma* samples may be applied to the application face of the membrane in order to produce the detectable signal on the indicator face as a result of activation of the substrate by the coagulation pathway component.

10. *A test article as in claim 1, wherein the solid phase matrix is a bibulous structure comprising a porous membrane structure composed of a hydrophilic and non-swellable polymeric matrix material having pore dimensions which permit entry of blood plasma and proteins while excluding blood cells.*

11. *A test article as in claim 1, wherein the solid phase matrix is a non-bibulous structure comprising an impermeable structure having at least one discrete capillary flow path.*

12. *A test article as in claim 11, wherein the capillary flow path is for receiving a blood or plasma sample.*

13. *A test article as in claim 11, wherein the dry thromboplastin and the coagulation neutral agents are coated on a wall of the capillary flow path so that the thromboplastin is rehydrated as a sample is drawn therethrough by capillary action.*

14. *A test article as in claim 1, wherein the coagulation neutral agents are selected from the group consisting of bovine serum albumin and polyvinyl alcohol.*

15. *An improved prothrombin time assay as in claim 7, wherein the solid phase matrix is a bibulous structure comprising a porous membrane structure composed of a hydrophilic and non-swellable polymeric matrix material having pore dimensions which permit entry of blood plasma and proteins while excluding blood cells.*

16. *An improved prothrombin time assay as in claim 7, wherein the solid phase matrix is a non-bibulous structure comprising an impermeable structure having at least one discrete capillary flow path.*

17. *An improved prothrombin time assay as in claim 16, wherein the capillary flow path is for receiving the blood or plasma sample.*

18. *An improved prothrombin time assay as in claim 16, wherein the dry thromboplastin and the coagulation neutral agent are coated on a wall of the capillary flow path so that the thromboplastin is rehydrated as a sample is drawn therethrough by capillary action.*

19. *An improved prothrombin time assay as in claim 7, wherein the coagulation neutral agent is selected from the group consisting of bovine serum albumin and polyvinyl alcohol.*

* * * * *